(12) United States Patent
Rupnik

(10) Patent No.: US 11,739,007 B2
(45) Date of Patent: Aug. 29, 2023

(54) REACTOR FOR PROXIMAL AND PERPENDICULAR RADIATION OF ELECTROMAGNETIC WAVES ON A THIN FLUID BED

(71) Applicant: Carlo Rupnik, Budva (ME)

(72) Inventor: Carlo Rupnik, Budva (ME)

(73) Assignee: Carlo Rupnik, Budva (ME)

( * ) Notice: Subject to any disclaimer, the term of this patent is extended or adjusted under 35 U.S.C. 154(b) by 0 days.

(21) Appl. No.: 16/647,482

(22) PCT Filed: Sep. 14, 2018

(86) PCT No.: PCT/IB2018/057072
§ 371 (c)(1),
(2) Date: Mar. 14, 2020

(87) PCT Pub. No.: WO2019/053656
PCT Pub. Date: Mar. 21, 2019

(65) Prior Publication Data
US 2020/0377385 A1    Dec. 3, 2020

(30) Foreign Application Priority Data

Sep. 14, 2017    (IT) .................. 102017000102853

(51) Int. Cl.
*C02F 1/32*    (2023.01)
*A23C 3/07*    (2006.01)
(Continued)

(52) U.S. Cl.
CPC .............. *C02F 1/325* (2013.01); *A23C 3/076* (2013.01); *A61L 2/085* (2013.01); *A61L 2/10* (2013.01);
(Continued)

(58) Field of Classification Search
CPC ................. C02F 1/325; C02F 2201/08; C02F 2201/009; C02F 2201/3222;
(Continued)

(56) References Cited

U.S. PATENT DOCUMENTS

2019/0014618 A1* 1/2019 Rupnik ................... C02F 1/325

FOREIGN PATENT DOCUMENTS

CN    106186174 A    12/2016
CN    2017-136438 A1    5/2017
(Continued)

*Primary Examiner* — Nicole M Ippolito

(57) ABSTRACT

The invention relates to an electromagnetic wave irradiation reactor (fixed, mobile or portable) suitable for the physical, dynamic, continuous conditioning of materials having the ability to absorb electromagnetic radiation, which need to be treated through electromagnetic irradiation, without coming into contact with the electromagnetic source. In particular, this invention aims to treat those materials which tend to reflect such radiations, which are translucent or difficult to penetrate to irradiation or simply dirty. The invention mainly exploits the postulates of Lambert, and Stefan-Boltzmann, that is, the physical assumptions of the transmission of electromagnetic energy by radiation and in particular the angle, concentration and proximity of the emission of energy between emitter and receiver (which varies with the square of the distance) and the intensity of the emission (which varies with the 4th power of the temperature).

8 Claims, 10 Drawing Sheets

Figure 1B:
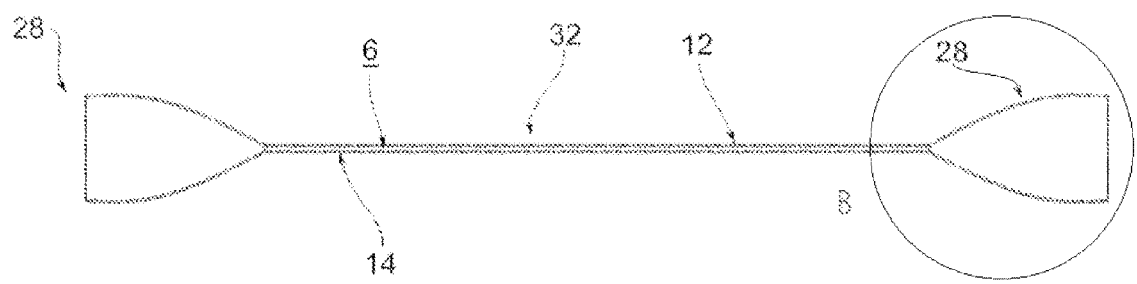

(51) Int. Cl.
*A61L 2/00* (2006.01)
*A61L 11/00* (2006.01)
*H05B 3/00* (2006.01)
*A61L 2/08* (2006.01)
*A61L 2/10* (2006.01)
*A61L 2/26* (2006.01)

(52) U.S. Cl.
CPC .................. *A61L 2/26* (2013.01); *A61L 11/00* (2013.01); *H05B 3/0052* (2013.01); *A61L 2202/11* (2013.01); *A61L 2202/122* (2013.01); *C02F 2201/008* (2013.01); *C02F 2201/009* (2013.01); *C02F 2201/3222* (2013.01); *C02F 2201/3228* (2013.01); *C02F 2303/04* (2013.01)

(58) Field of Classification Search
CPC ......... C02F 2201/3228; C02F 2303/04; A23C 3/076; A61L 2/085; A61L 2/10; A61L 2/26; A61L 11/00; A61L 2202/11; A61L 2202/122; H05B 3/0052
USPC ...... 250/436, 453.11, 454.11, 455.11, 493.1, 250/504 R
See application file for complete search history.

(56) References Cited

FOREIGN PATENT DOCUMENTS

| | | |
|---|---|---|
| DE | 2014050612 A1 | 2/2014 |
| DE | 2016137528 A1 | 5/2016 |
| DE | 2017144898 A1 | 5/2017 |

\* cited by examiner

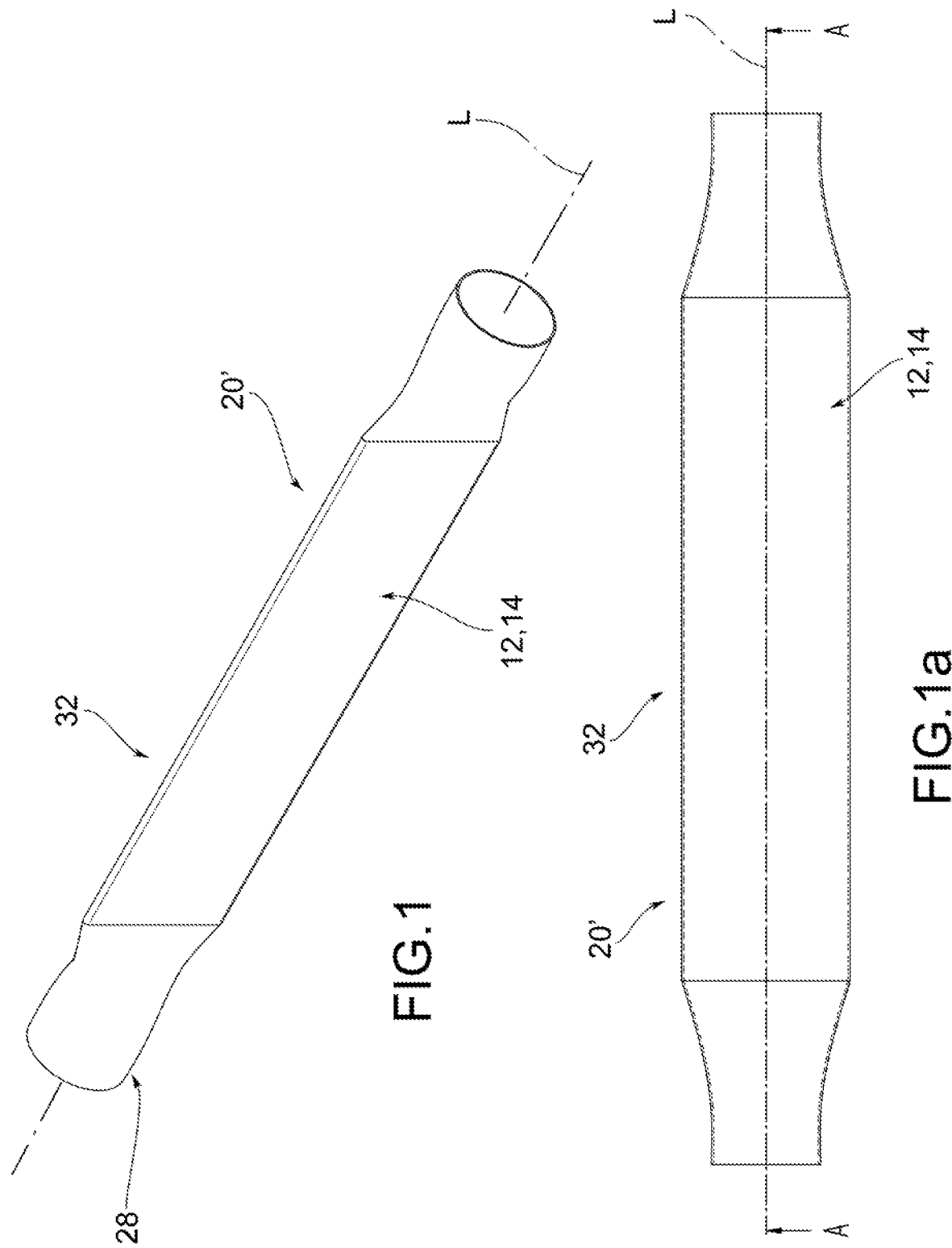

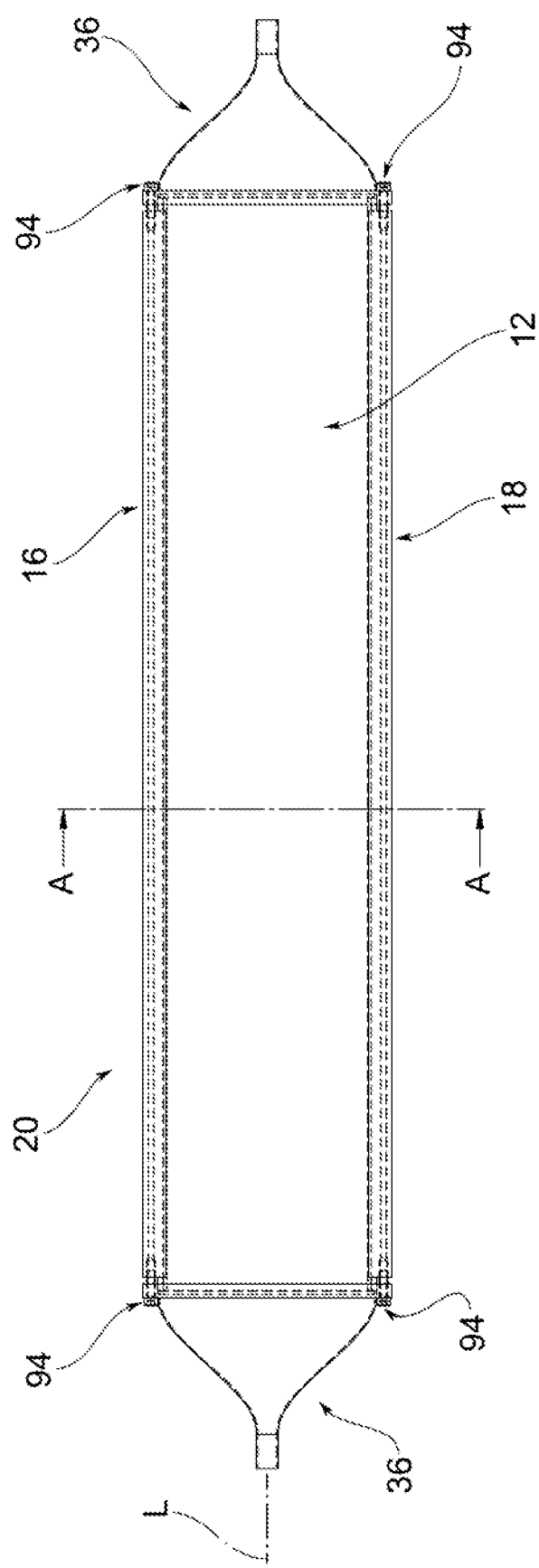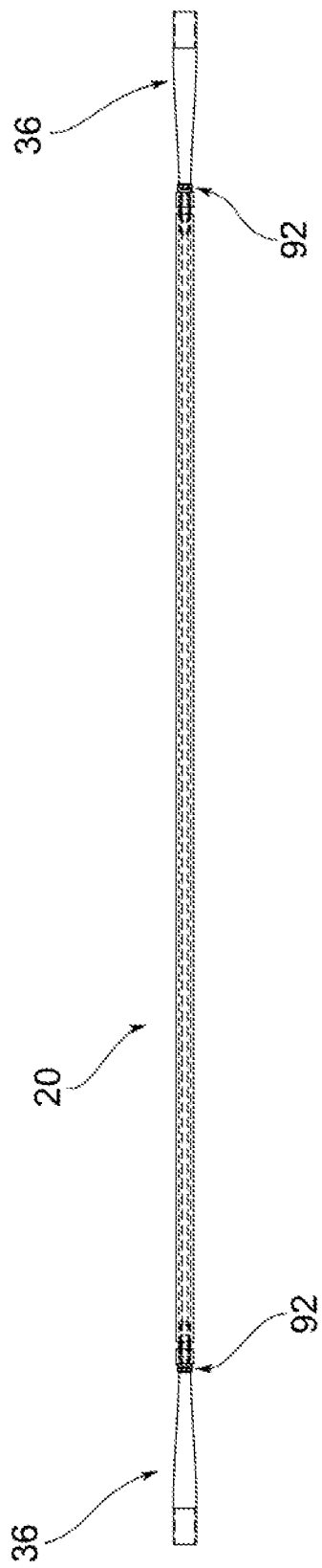
FIG.4
FIG.4a

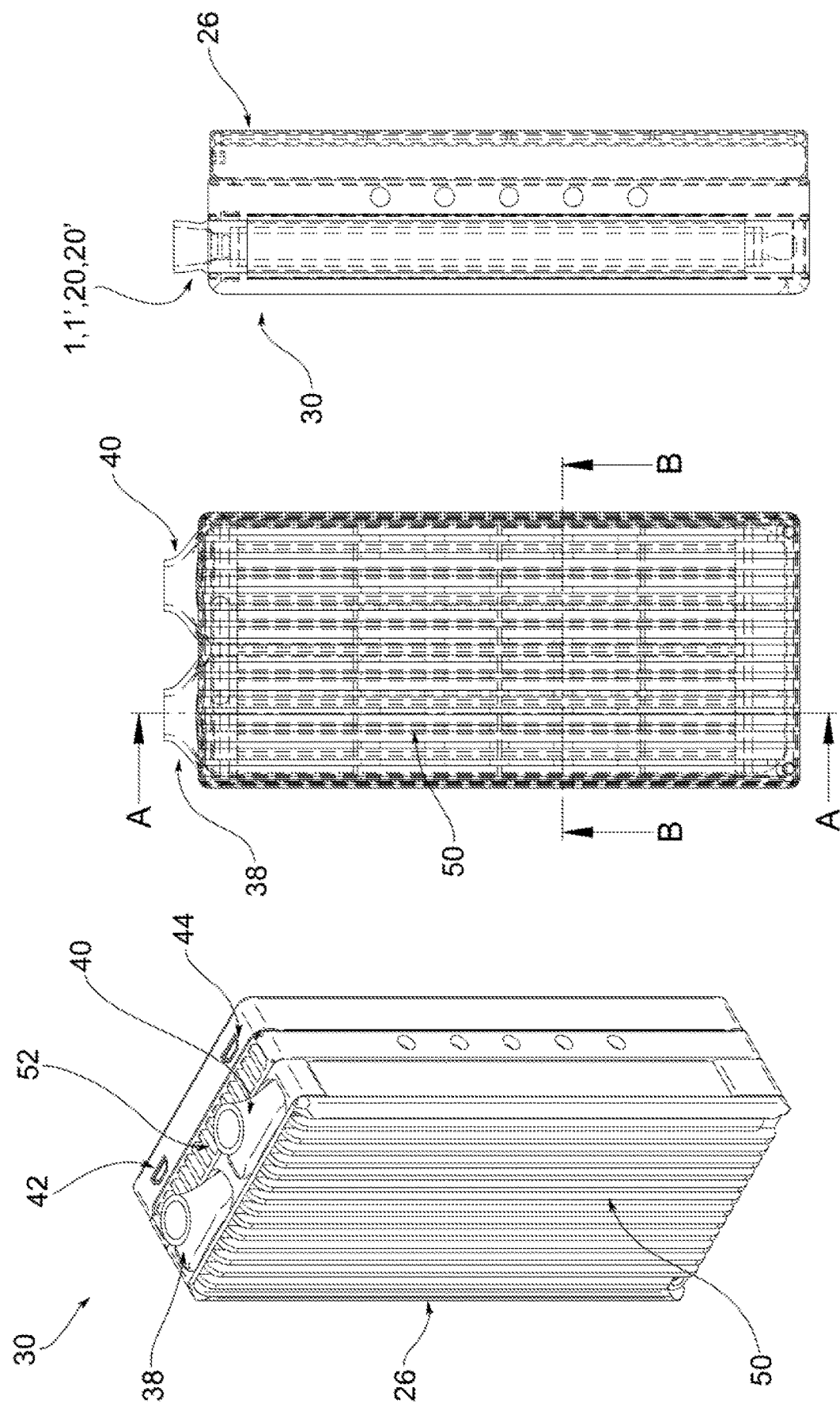

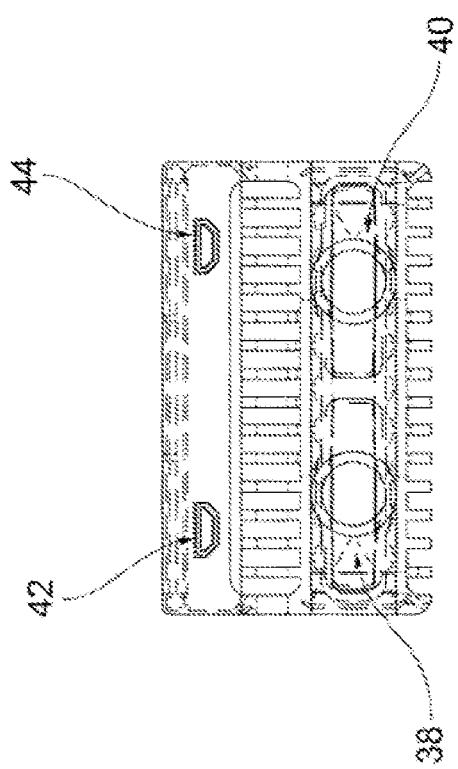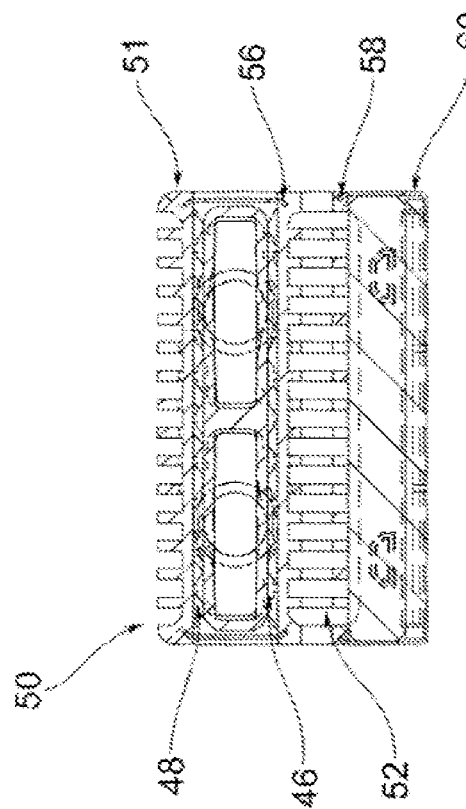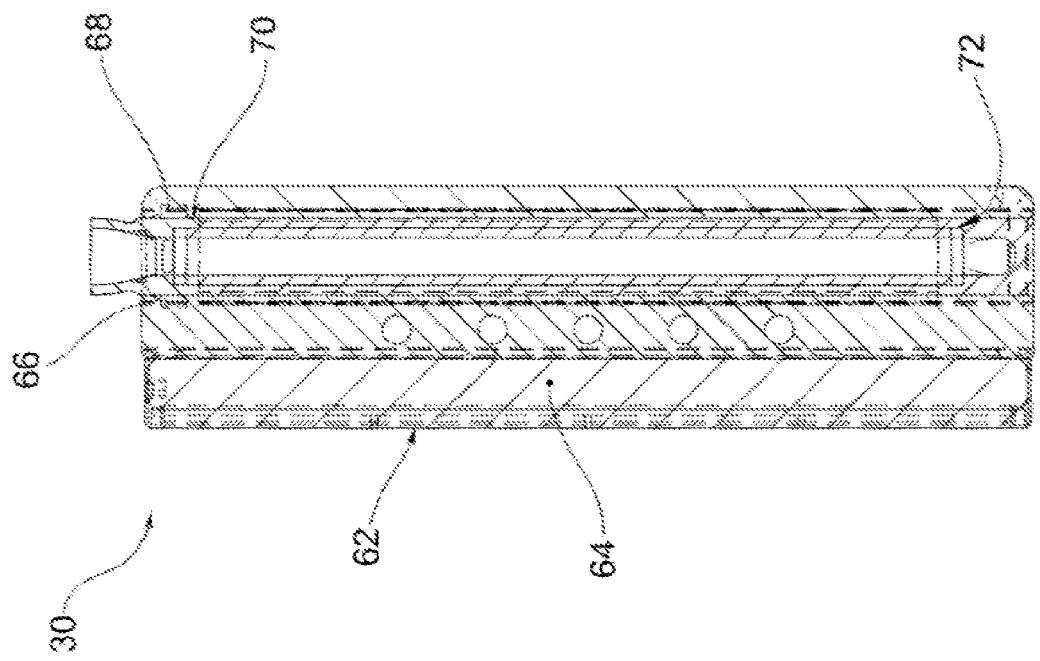

REACTOR FOR PROXIMAL AND PERPENDICULAR RADIATION OF ELECTROMAGNETIC WAVES ON A THIN FLUID BED

The present invention relates to a reactor for irradiation of electromagnetic waves.

The use of electromagnetic wave (EMW) irradiation systems, based on plates with or without the aid of quartz tubes provided with internal resistance IR or with mercury emitters for UV, as well as armoured resistors, or the lamps made with quartz tubes are widely used systems, known both to industry and to the so-called "consumer appliances" devices such as, for example, cooking plates, stoves, wall and ceiling heaters, convector heaters and UV-C sterilizers for environment, for tools, water, milk, wine, beer, aquariums, etc.

In a general sense, the present invention grounds its bases on well known subjects to the art and some patents have even been released in the nineteenth century (i.e. 27 Jan. 1898—U.S. Pat. No. 631,360 A).

It is useful to observe that, notwithstanding the irradiation principle and the construction techniques are the same, the state of the art is better described in the group of EMW frequencies embraced by the invention described herein: it is about IR heating systems and of short wavelength UV irradiation systems. They are located at the two ends of the EMW scale which are of interest to the present invention, that is, the electromagnetic field comprehended between 100 nanometers (UV-C) and the millimeter (IR-C) of wavelength.

In addition to the patent application WO2017115394, titled "Tubular concentrator for concentric irradiation of electromagnetic waves", filed by the same Applicant, it is possible to analyse the state of the art in the main fields of use of the invention, namely:

Ultraviolet Applications

UV sterilization has been known for a long time and is normally used in many fields ranging from the treatment of drinking water to the waste one and to the disinfection of surgical operating rooms and equipment contained therein and used, as well as in the treatment of other beverages for human and animal consumption.

For current uses, the conventional technique generally involves the construction of lamps very similar to fluorescent lamps or, in recent history, by means of light emitting diodes, commonly called LEDs (light emitting diodes) which are still not very common, however, as a consequence of the low energy yields when compared to the now common LEDs that can be used for lighting.

The so-called "conventional" lamps, at low and medium pressure, are built using the ionization of mercury vaporous but, instead of using a conventional boron-silicate glass that would be opaque at ultraviolet wavelengths, they use tubes in finest pure fused quartz (SiO2) as containers of the lamp itself: in other words, the lamps used for germicidal use are enclosed in an ampoule of extra pure fused quartz.

The use of such lamps for liquids is basically carried out in two ways:
1. the positioning of the lamps above the materials to be sterilized or, generally, in the environments to be sterilized;
2. they are inserted in a container (generally) of steel in the shape of a tube with two orthogonal fittings placed at the ends of the cylindrical outer part, suitable for inlet and outlet of fluids, in order to shield the harmful outside UV-C irradiation useful for the sterilizing effect. The centre of the tube is reserved for the insertion of the germicidal lamp which protrudes from the two ends of the cylinder.

It is therefore normal to observe that, in the first system (external positioning) the emission points remain particularly far from the matters to be sterilized and sterilization takes place from a single angle (except multiplying the lamps) while in the second solution (container), in addition to having only one angle of radiant light source, the liquids are forced to particular deviations which cause pressure drops in the flow pressure of the circulating fluids, as the homogeneity of the treatment remains incomplete for the different distances of absorption of the radiations of the liquids with respect to the emission source.

Some more current embodiments, such as those described in the patent document SurePure Turbulator, later SPT WO2016092488A1, and Ultra Violet/Thermal Pasteurization by Ypsicon, later UVTPY, two systems dedicated to liquids, in particular milk, are both close to today's invention but still different in the substantial elements. The first, SPT WO2016092488A1, addresses the problem of the difficult UV penetration of milk through appropriate helical grooves that provide milk with a whirling motion, offering greater exposure of the product to the internal UV lamp; the second UVTPY, although it offers some double exposure, internal and external, to the liquid to be treated and reduces the space between the tube and the lamp still does not present all the features of functionality and efficiency offered by the present invention. In fact, in addition to using conventional mercury/xenon lamps instead of LEDs, both of them do not really consider the concepts of proximity of EMW emitters to receivers, such as milk, and also do not associate the necessary contemporaneousness of the reflecting walls to the wavelengths used in order to increase reactor efficiency.

Infrared

In the infrared field the current state of science and industrial production knows tubular or microtubular heaters used in many industrial environments, such as hot runner injection systems (so-called "Hot Runners") for plastic molding, for vulcanization presses, for welding machines and hot marking machines, as well as for the heating of vacuum ovens, sterilization systems and many other systems that require small heating pipes.

EP0287772 A1 describes a heating element for domestic electrical equipment, which foresees the water to be heated to pass inside a resistor rather than outside.

U.S. Pat. No. 6,674,054B2 discloses a method and an apparatus for heating a solution.

The object of the present invention is to propose a reactor of the type described for example in the aforementioned patent application WO2017115394A1, but having improved performance, and an even more effective detail in terms of treatment of the substance to be treated.

This object is achieved, according to claim 1, with a tubular reactor 1, 1' by irradiation of EMWs (ElectroMagnetic Waves) of substantially cylindrical shape, comprising:
  a pair of concentric tubes 2, 4 extending in longitudinal direction L and comprising an outer tube 2, defined by an inner wall of outer tube 2 and by an outer wall of outer tube 2, and an inner tube 4, defined by an inner wall of inner tube 4 and by an outer wall of inner tube 4, said outer 2 and inner 4 tubes being made of transparent material to the EMWs, for example quartz, being open at both ends, and forming a gap 6 defined by the inner wall of outer tube 2 and by the outer wall of inner tube 4, said gap 6 being suitable for the passage of a material to be treated, for example in solid, liquid, gaseous and/or powdery form;

a couple of opposing EMW emission sources 8, 10, comprising an external source 10 and an internal source 8 formed by at least one EMW emitter, the external source 10 winding the outer wall of outer tube 2 with the face of EMW emission of the external source 10 facing inwardly of the reactor 1, 1', the internal source 8 winding the inner wall of inner tube 4 with the EMW emission face of the internal source 8 facing outwardly of the reactor 1, 1', said emission sources 8, 10 emitting EMWs with wavelengths comprised between the ultraviolet (UV) and infrared (IR) rays, so as to radiate perpendicularly, with respect to the longitudinal direction L of the reactor development, the material to be treated flowing in the gap 6.

In a variant embodiment, a lamellar reactor 20 is proposed for irradiation of EMWs (ElectroMagnetic Waves) comprising:

a couple of flat plates 12, 14 of rectangular shape and extending in longitudinal direction L, said flat plates 12, 14 being made of transparent material to the EMWs, for example quartz, and being arranged without contact one above the other by means of a pair of profiles 16, 18 suitable for engaging with the longitudinal edges of the flat plates 12, 14, said flat plates 12, 14 and said profiles 16, 18 delimiting an external portion to the reactor and an internal portion the reactor, said internal portion defining a gap 6 open at both ends and suitable for the passage of a thin film of a material to be treated, for example in solid, liquid, gaseous and/or powdery form;

a couple of opposed EMW emission sources 8, 10, said emitters 8, 10 by coating the surface of the pair of flat plates 12, 14 defining the external portion to the reactor 20 and emitting EMW towards the internal portion of the reactor 20, in order to radiate perpendicularly to the longitudinal direction L of the reactor development, the gap 6 where the material to be treated flows, with EMW of wavelengths included between the ultraviolet rays (UV) and the infrared rays (IR).

In a preferred embodiment, the reactor 1, 1' comprising a pair of reflectors 22, 24, in which a first reflector 22 of said pair of reflectors 22, 24 covers a first emission source 10 of the two emission sources and wherein the second reflector 24 of said pair of reflectors 22, 24 covers the second emission source 8 of the pair of emission sources, said first 22 and second 24 reflector being suitable for the reflection of EMWs towards the gap 6.

In one embodiment, the pair of reflectors 22, 24 is made of a material having a reflection coefficient of the EMWs between 0.5 and 1.

In one embodiment, the pair of reflectors 22, 24 are made of a material having a thermal conductivity lower than 5 W/m·K calculated at 20° C.

In one embodiment, the emission sources 8, 10 radiate EMWs with wavelengths different from one another.

According to an embodiment, the distance between the material to be treated and any of the two emission sources 8, 10 is between 50 micrometers and 30 millimetres.

For example, concentric tubes 2, 4 or flat plates 12, 14 have a thickness less than or equal to 1 millimetre.

In one embodiment, each EMW emission source 8, 10 comprises a plurality of EMW emitters.

Preferably, the EMW emitters of an emission source (8 and/or 10) are arranged so as to form an emission layer.

Furthermore, it is also object of the invention a device for the disinfection of fluids 30 made inside a transportable casing 26 comprising a tubular reactor 1, 1' and/or a lamellar reactor 20, 20' as described above and suitable electric power supplies for the operation of said reactors 1, 1', 20, 20'.

In an embodiment, it is proposed an electromagnetic reactor for double irradiation, perpendicular and close up of electromagnetic waves at high efficiency on a gap 6 or on a thin film, consisting of at least one gap 6 completely covered on the outside, above and below or inside and outside, from sources 8, EMW radiators, shielded from the outside, to treat or condition a variety of materials, whether in liquid, gaseous, powdery or pulp form, the sections of which are represented by the accompanying drawings.

The reactor:

i. it mainly uses electromagnetic radiation as a means of energy transfer, ii. it irradiates mainly electromagnetic energy in close range, in the fields between 100 nanometres (UV-C) and the millimetre (IR-C) of wavelength, iii. it irradiates the flowing material within the system in such a way:
1. very close (extreme proximity),
2. perpendicular,
3. double;

iv. optionally, with the emitter of electromagnetic waves wound in contact with a tube that can have a wall of less than one millimetre thickness;

v. also suitable to work under vacuum or pressure;

vi. optionally be free of physical contact with the materials to be treated;

vii. indiscriminately achievable in fixed form, mobile or portable.

In one embodiment, the reactor comprises:

i. at least one gap 6 open at both ends to allow passage of the materials to be treated;

ii. in which the walls of the gap 6 are transparent to the wavelengths involved, and are for example made of very pure quartz ($SiO_2$), so that the same EMWs are attenuated as little as possible by the walls of said gap 6, which may also being formed by two tubes 2, 4, during the process of transferring the electromagnetic energy radiated from the emitter to the material to be treated;

iii. at least one EMW generator;

iv. at least one emitter (or source) of electromagnetic waves represented for example by a coil of resistive wire, from silicon carbide or other resistive material, as well as by a sequence of light-emitting diodes (LEDs), in its various single forms, in groups, SMD or COB, of the desired frequencies, which surmounts, by wrapping them, the outer walls of the gap 6 and emits the radiation towards the inside of the gap 6 itself. v. at least one layer of reflecting material (or reflector) at the involved wavelengths, located outside the radiation source, so as to encapsulate and contain as much as possible inside the reactor the energy necessary for operation;

vi. at least one layer subsequent to the previous one (v.) made with suitable materials which have the characteristic of being able to dissipate excess heat when the EMW emitter is destined to produce UV while having instead the characteristic of containing the heat inside the reactor when the invention is working on the infrared or near infrared wavelengths. For containment or high insulating power we mean those materials that can offer low thermal conductivity, less than 5 W/m·K at 20° C., in addition to a high reflection, close to an index 1, combined with the reduced or almost absent transmission and/or electromagnetic absorption; if the need is to disperse the heat generated by the UV emitters, the thermal conductivity should instead be as high as possible, i.e. with values above 200 W/m·K at 20° C.

For ideal values of reflective functions we mean a coefficient of physical reflection tending towards the unit, associated with the transmission and absorption coefficients which tend to be close to zero, having regard to the wavelengths involved; the case could be to use special opaque quartz artifices made to reflect electromagnetic waves.

Within the gap 6 created for example with quartz walls, various materials can flow, of various nature and features such as: liquids, powders, gases, slurries, which are irradiated by a perpendicular beam of electromagnetic waves generated by an emitter resting on the outer surface of the walls of the gap 6 itself with the aim of reducing as far as possible the distance between said emitter and the material to be treated that passes inside said quartz gap 6 and this in order to maximize exploitation of the Lambertian theories and by Stefan-Boltzmann.

For close distances to the gap 6 and between the emitter and receiver materials are meant measures between the quasi-contact, or 50 micrometers and 30 millimetres, which can be increased as commensurate with the powers at stake, or in the presence of higher powers issued, there may be greater relative distances; in any case, "near contact" is preferable.

In one embodiment, the external protection is made of materials having an electromagnetic reflection coefficient in the range of the frequencies involved, close to the unit and in any case higher than 0.5; electromagnetic reflection is intended for the wavelengths of the emitter.

In one embodiment, the external protection associates a high insulating power to the reflecting power. In other words, in addition to the reflection mentioned above, the external protection also offers thermal insulation, namely it has a low thermal conductivity at 20° C. (lambda−1) between 0 and 5 W/m*K.

In one embodiment, the reactor is incorporated inside an efficient insulating cup which has the task of reducing the outward dispersions of electromagnetic radiations or simply of thermal energy. The materials of the insulating cup will be chosen according to the machine design temperatures and frequencies.

In one embodiment, the reactor is suitable for working in the absence of gas (vacuum) or in the presence of specific gases as well as liquids.

In one embodiment, the reactor employs EMW emission sources which each form an emitter layer so thick as to avoid the need for screens of any kind, for example reflecting or insulating layers.

In one embodiment, the reactor operates with more than one frequency, for example with emission sources emitting both EMW IR and UV simultaneously.

Figure 1D:
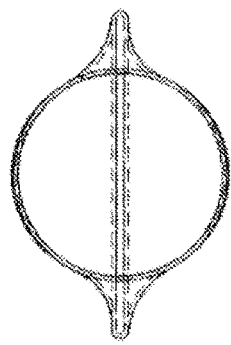
Figure 1C:
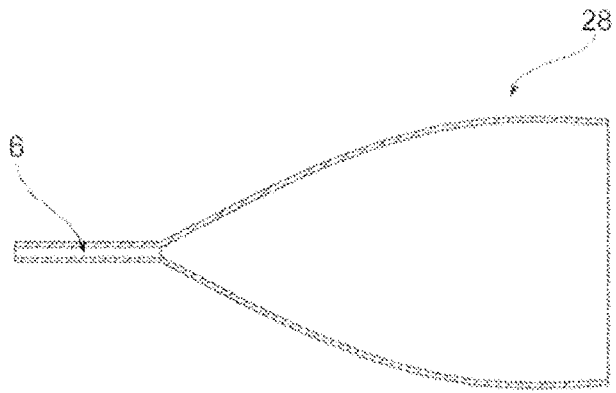
Figure 2:
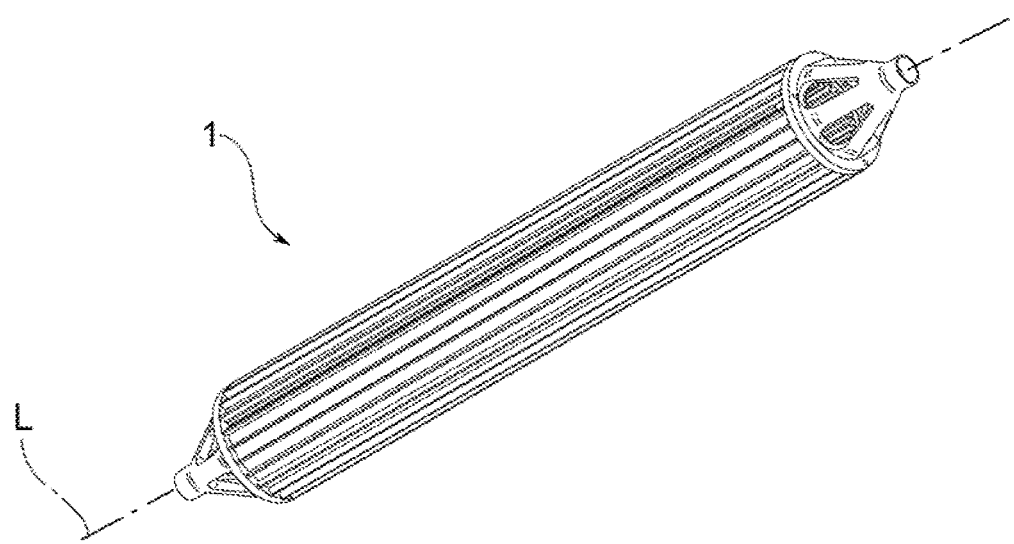
Figure 2A:
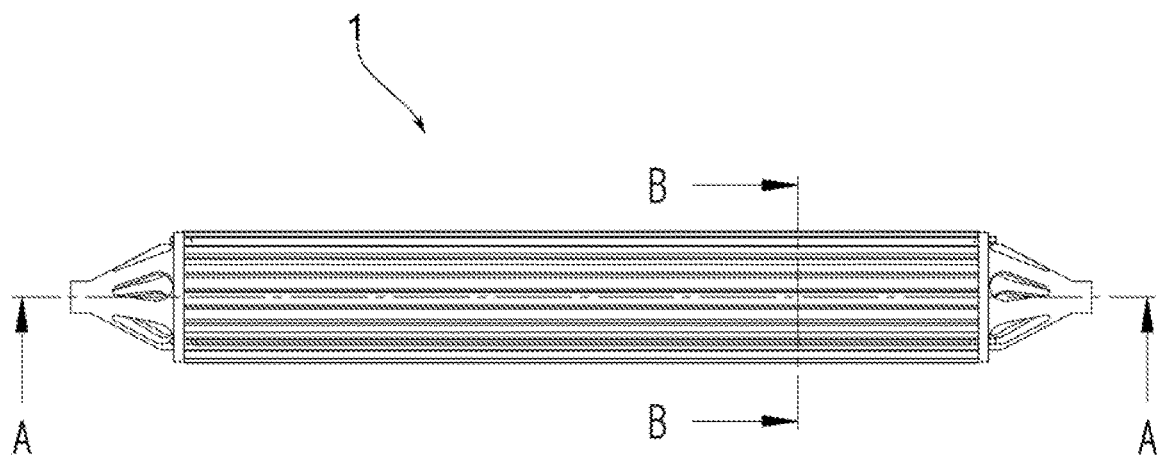
Figure 2B:
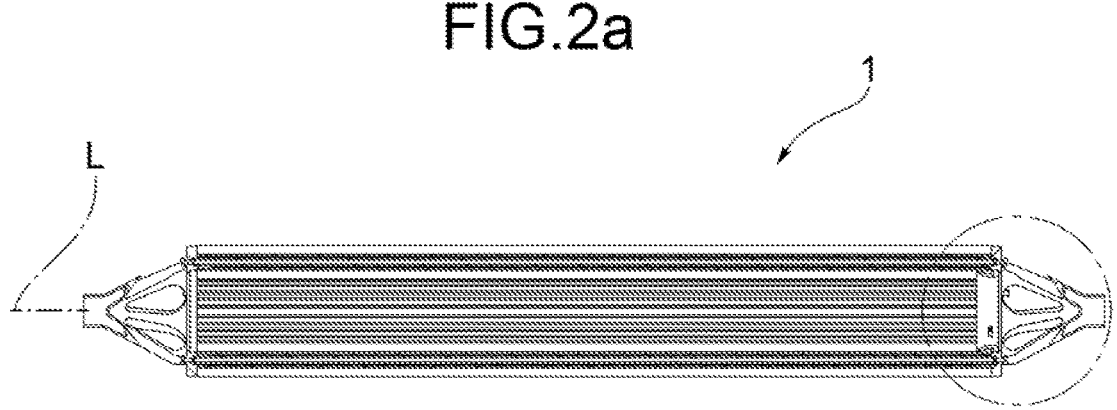
Figure 2D:
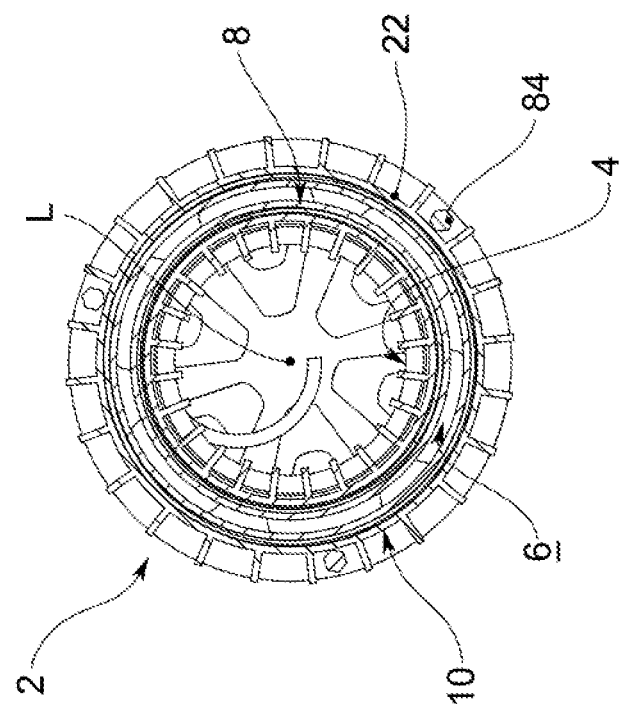
Figure 2E:
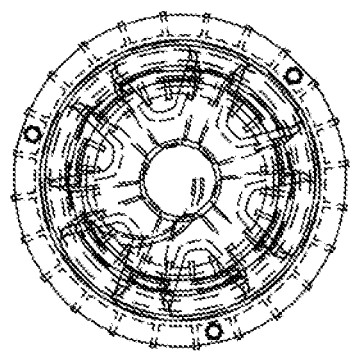
Figure 2C:
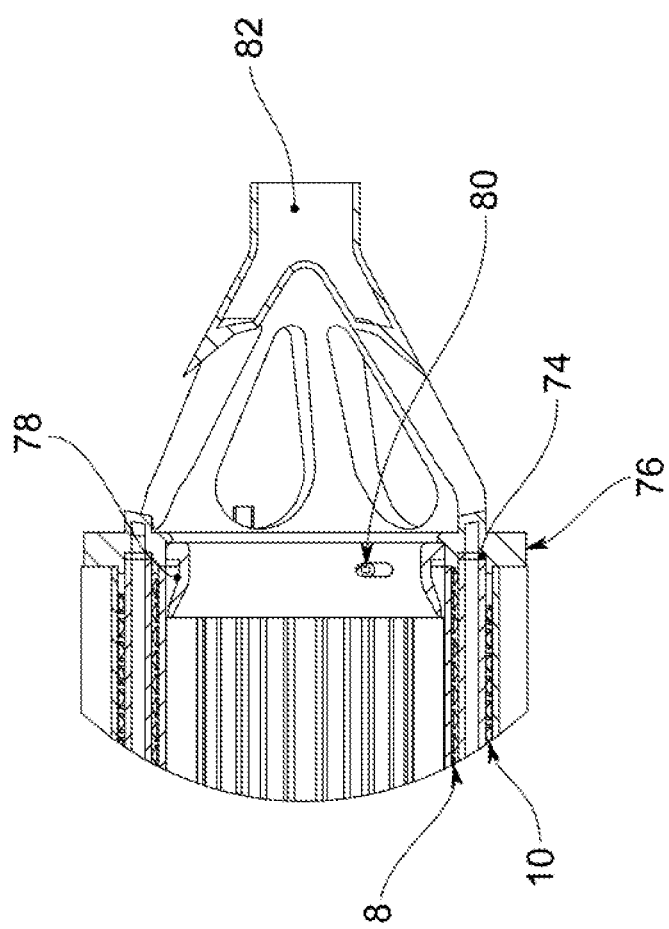
Figure 3:
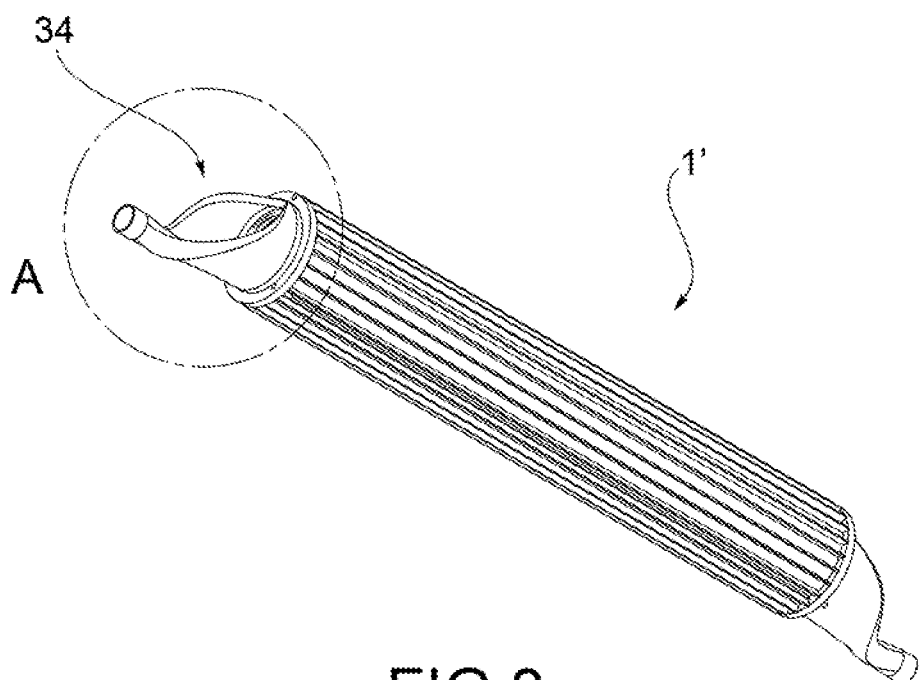
Figure 3A:
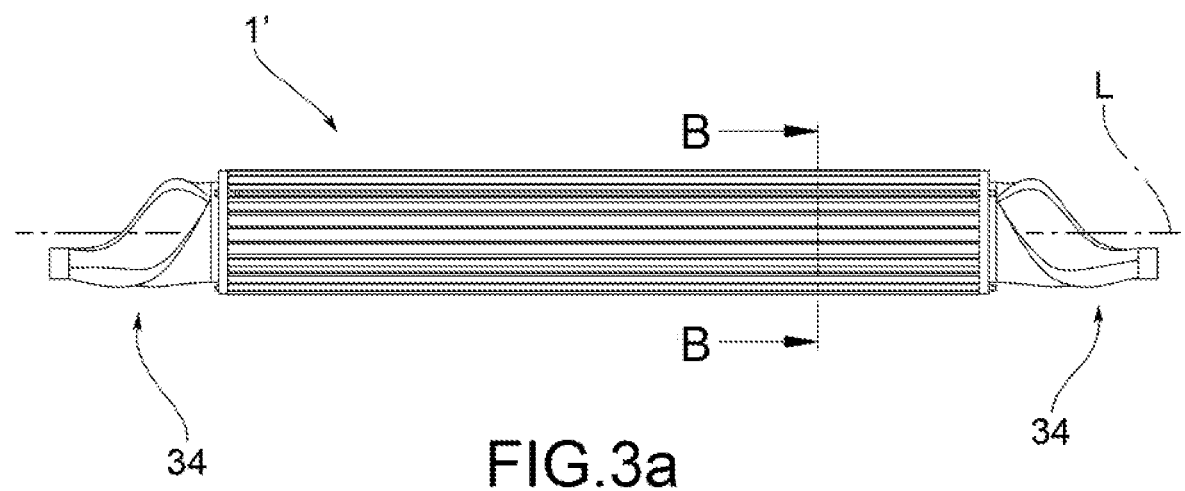
Figure 3B:
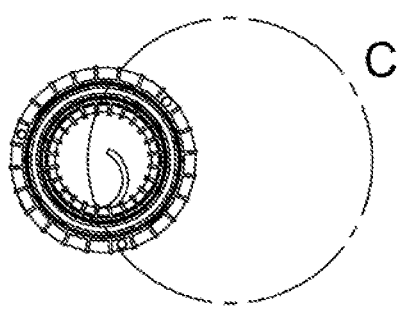
Figure 3D:
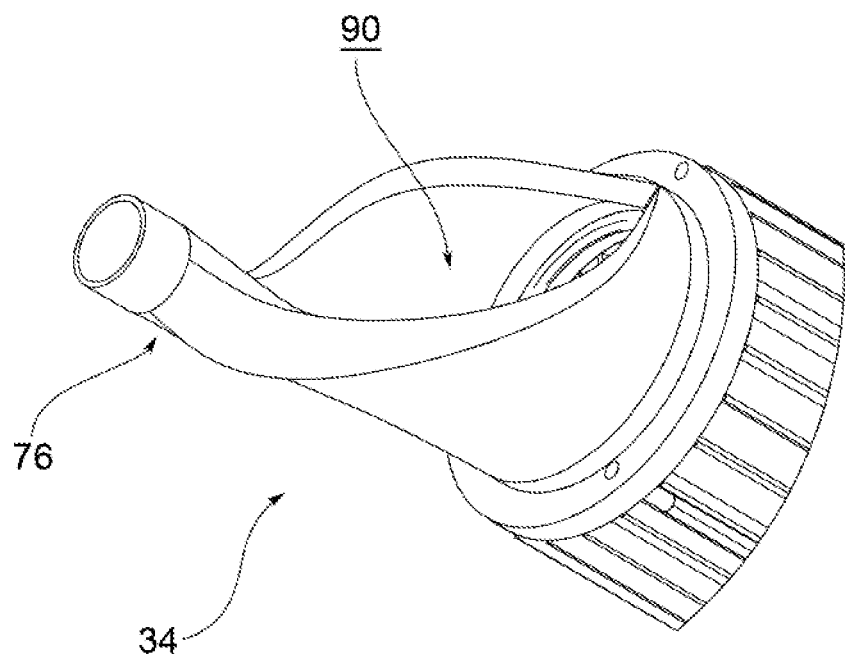
Figure 3C:
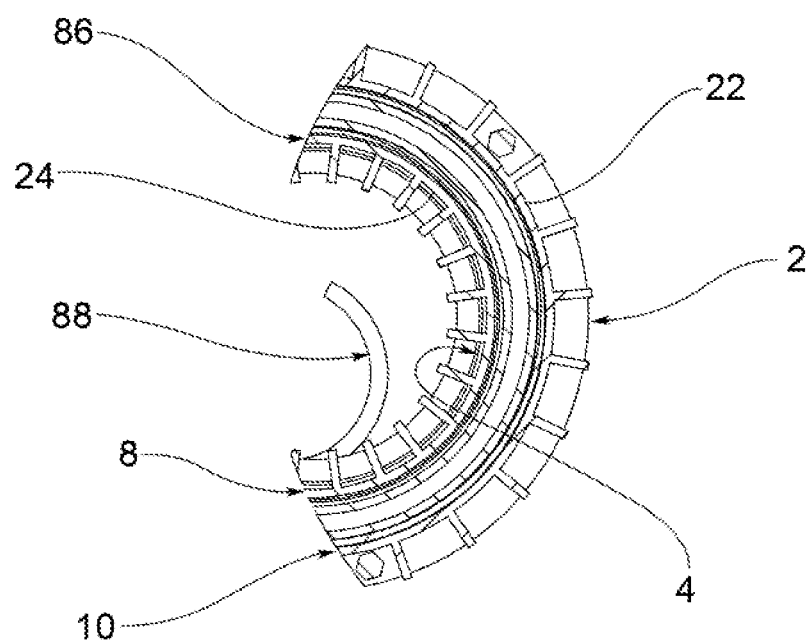
Figure 4D:
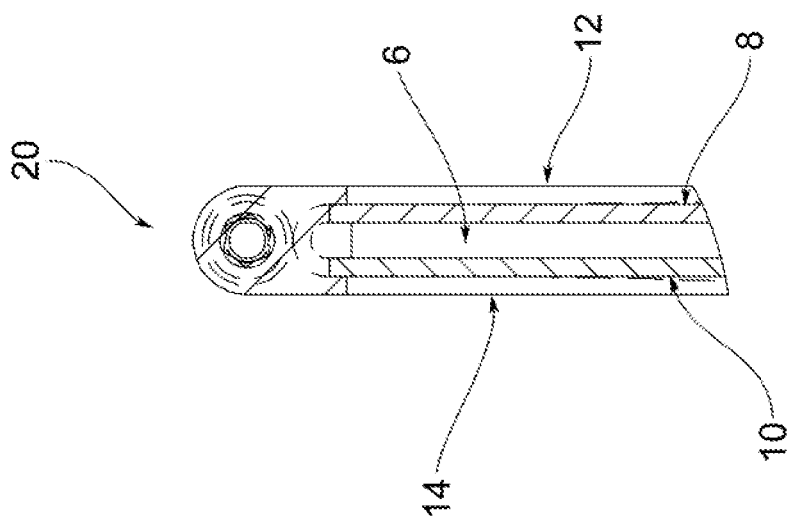
Figure 4C:
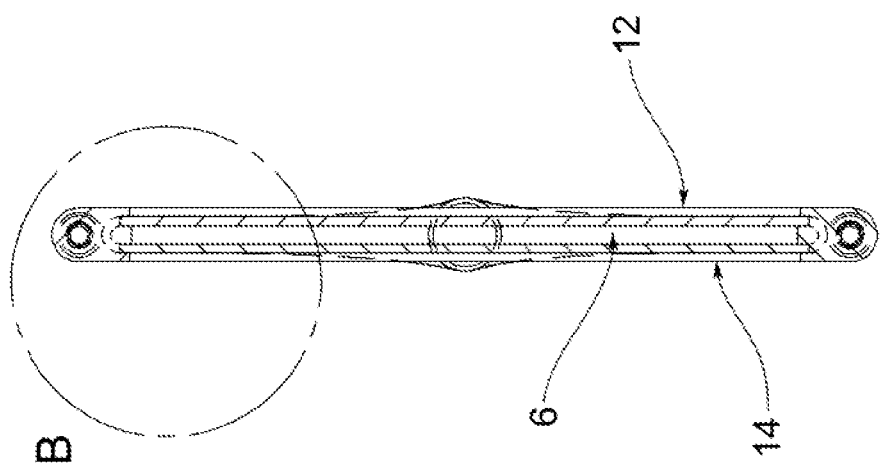
Figure 4B:
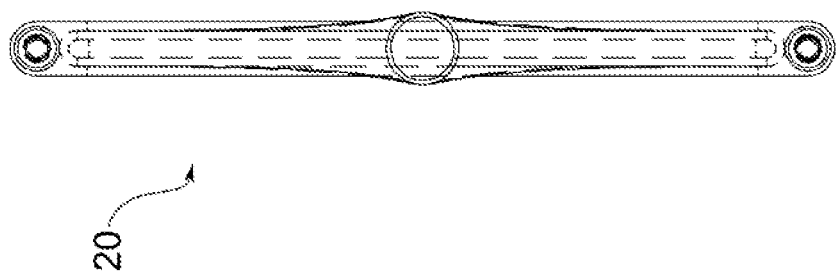

Further characteristics and advantages of the reactor according to the invention will be evident from the following description of its embodiments, given by way of non-limiting example, with reference to the attached figures, in which:

FIGS. 1, 1*a* and 1*b* show, in a perspective view, in front view and in axial section, the geometric shape of a reactor 20' according to the invention in an embodiment;

FIG. 1*c* is an enlarged view of the detail B circled in FIG. 1*b*;

FIG. 1*d* is an end view of the reactor of the previous figures;

FIGS. 2 and 2*a* show, in a perspective view and in front view, a reactor according to the invention in a first concrete embodiment;

FIG. 2*b* is a view in partial axial section of the reactor of FIG. 2;

FIG. 2*c* is an enlarged view of the detail C circled in FIG. 2*b*;

FIG. 2*d* is a cross-section of the reactor along the line B-B of FIG. 2*a*;

FIG. 2*e* is an end view of the reactor of FIG. 2;

FIGS. 3 and 3*a* show, in a perspective view and in front view, a reactor according to the invention in a second concrete embodiment;

FIG. 3*b* is a cross-section of the reactor along the line B-B of FIG. 3*a*;

FIG. 3*c* is an enlarged view of the detail C circled in FIG. 3*b*;

FIG. 3*d* is an enlarged view of detail A circled in FIG. 3;

FIGS. 4-4*b* are orthogonal views of a reactor in a third practical embodiment;

FIG. 4*c* is a cross-section of the reactor along line A-A of FIG. 4;

FIG. 4*d* is an enlarged view of the detail B circled in FIG. 4*c*;

FIGS. 5-5*c* are a perspective view and orthogonal views of a device for transportable fluid disinfection 30;

FIG. 5*d* is a cross-section of the device along line A-A of FIG. 5*a*; and FIG. 5*e* is a cross-section of the device along the line B-B of FIG. 5*a*.

In an embodiment illustrated in FIGS. 1-1*d*, the reactor has cylindrical end portions 28 and a central portion 32, which extends most of the length of the reactor 20', so as to create more thin layers of materials that can be treated more easily with less powerful emitters, due to the smaller thickness of the base fluid of the treated materials flowing into the reactor 20'. Moreover, the invention, by characterizing the appearance of the thin fluid bed, always presents the construction of a narrow gap 6 proportional to the needs of the material to be treated.

In fact, there are materials that tend to reflect the EMWs, which are therefore difficult to penetrate to the point that already a couple of millimetres of thickness are sufficient to prevent the fluid from crossing the EMWs. The invention therefore aims to be a system to overcome the aforementioned drawback.

In an embodiment illustrated in FIGS. 2-2*e*, the necessary narrow section to be irradiated is obtained by means of the appropriate coupling of two concentric tubes 2, 4, for example of quartz, with the emission sources 8, 10 which are made of two different opposing layers, the first 8 of which is provided to be applied in the inner tube 4, arranged in its interior with the emissive face facing the outside of said tube 4.

The second emissive layer 10 is instead placed outside the outer tube 2 with the emissive part facing the inner tube 2, so as to direct the emission towards the other described irradiator 8, placed inside.

In the gap 6 created between the two tubes 2, 4 there are therefore two contrasting flows of the EMW which both perpendicularly invest the material to be treated which flows in said gap 6. Obviously, these contrasting flows may also be of different wave lengths in the same reactor: for example one UV and the other IR. It is possible to notice how the proximity of the emitters is right next to the gap 6.

The same reactor can be made with different terminals, depending on the needs of the plant.

In the example of FIGS. 3-3d, the reactor has an offset inlet 34 with respect to the reactor body, i.e. an inlet radially offset from the longitudinal direction L which, according to an embodiment, constitutes an axis of symmetry of the tubes 2, 4. All reactors can be equipped with forced air cooling, optimized by means of a Coanda profile.

In an embodiment shown in FIGS. 4-4d, the same type of gap 6 is made of two flat quartz elements 12, 14 applied to a frame 16, 18 which holds them in position. The flow of liquids, gas or other is started by means of a round flange 36 which flattens to allow the liquid to penetrate the gap 6 formed by the two quartz surfaces on which a layer of material capable of emitting the requested EM radiation is applied (8, 10 visible in FIG. 4d), in turn coated with reflecting and dissipating material (UV) or reflecting and insulating material (IR)—the latter being not visible.

Also in this case, from the inside towards the outside of the reactor, it will be possible to see the following identical stratification for each part:
material to be treated
quartz layer
layer of emitting materials
layer of materials reflecting the wavelengths involved
heat sink layer or energy container, depending on the application.

A further version is represented by the portable device or model 30, shown in FIGS. 5-5e, mainly dedicated to the use of UV-C aimed at the disinfection of water. This portable version of the reactor is based exactly on the same principles as the previous ones but collects both the power supply and its reserve in the same casing, as well as a solar energy source and the necessary sockets to connect to both water and further electrical connection.

The portable device includes:
38 non potable water inlet
40 output of potable water
42 USB auxiliary power input
44 USB auxiliary power output
46 UV-C LED emitters (examples of source 8, 10 usable in a variant of the present invention)
48 UV-C LED emitters (examples of source 8, 10 usable in a variant of the present invention)
50 screen for reflection and heat dissipation led
52 screen for reflection and heat dissipation led
54 upper heat sink anchor slide
56 lower heat sink anchor slide
58 auxiliary battery anchor slide
60 solar cell battery power supply
1, 1', 20, 20' reactor or quartz container for water to be treated
1, 1', 20, 20' reactor or quartz container for water to be treated
62 Solar panel
64 Battery
66 Interlock and heatsinking buttonhole
68 Interlock and heatsinking buttonhole
70 sealing gasket
72 sealing gasket.

This version can also be used in complete absence of electric energy sources as long as the sun is available to transfer its energy through the appropriate solar cells incorporated in the invention.

These mentioned heaters for the use of the heating energy towards the inside of the machine itself, rather than the exterior, are perhaps the most similar applications to the present invention for the infrared part, but it is appropriate to consider that the today's invention associates at the same time:
viii. electromagnetic radiation;
ix. a frequency spectrum between the infrared and the ultraviolet;
x. the absence of filters between emitter and receiver;
xi. the intimate proximity between the emitter and the receiver;
xii. the reflection of the irradiation towards the inside of the machine;
xiii. the thermal insulation to limit the thermal conduction towards the outside or the exact opposite to disperse heat;
xiv. the very low thickness of the fluid bed created by the squizing of the tube, for example of quartz, in one case and by the presence of two very adjacent walls in the other.

As more analytically described below, in order to highlight the differences in the following fundamental constructive and concept details, the comparison shows that the known heaters:
i. they are made by using the so-called "armored resistances" instead of the visible resistive wire; in fact, in the aforementioned armored resistances (see EP 0287772A1) the resistive wire is drowned in a magnesium sand (MgO) which has the function of an electrical insulator as well as a thermal conductor;
ii. the EMW emission source does not appear to be so relatively "close" to the materials to be heated;
iii. they do not have a screen that reflects the EMWs of the infrared spectrum to the inside of the tube if not through a metal band that reflects the radiation but disperses by thermal conduction first and then through the radiating surface, a large amount of heat towards the external environment, reducing energy efficiency.
iv. they are structures conceived and designed for relatively limited lengths that cannot be reconciled with some industrial needs with dimensions well above the linear meter.
v. The above-mentioned U.S. Pat. No. 6,674,054 patent does not use irradiation if not in an embodiment in which it separates the heating tubes from the material to be heated which flows into the main tube, collecting the whole in a further tube, with greater distance, different incidence and lower efficiency, in addition to construction costs higher than today's invention;
vi. always the above patent, when it applies inductive resistances or conductors on the quartz tube, it does not transfer the energy by means of irradiation but by electromagnetic conduction or induction and in fact the quartz tube used is not specified (if translucent, transparent or opaque)

The combination of these differences involves a considerable diversity of the various electric machines mentioned, characterizing the innovation of the invention described here.

Today's invention in fact shows an irradiator, whose EMW emitter associates all the following characteristics at the same time:
i. it is adherent to the quartz substrate and therefore is close to the material to be treated;
ii. it has no shielding or filters covering the receiver material and it is instead equipped with a reflecting radiation screen, positioned around the emitter;
iii. it is equipped with a radiation reflecting screen, placed around the emitter to prevent and/or slow down the conduction and the radiation of energy;
iv. it is mainly based on radiation instead of conduction/convection/induction (although all are present);

v. it is useful to treat materials in solid, liquid, gaseous and powdery form;

vi. it is not intended solely for heat but for the entire range included in the IR-to-UV spectrum;

vii. due to its peculiar characteristics, it is aimed at energy saving, therefore at a high yield.

The particular nature of the emitter denotes a greater speed of entry at steady working temperature (lower thermal inertia): this happens precisely because it has no whatsoever screens or filters towards the direction of use, and because of the different arrangement of the resistive material which is placed "naked" around or above the fused quartz tube rather than being housed inside or drowned in the magnesia sand in a steel casing. The tubular heaters known in the current state of the art are based on the armored resistances which interpose two different screens between the resistive wire, source of infrared emission, and the material to be heated; these screens are constituted by the magnesium oxide layer (MgO) used to electrically insulate the resistive wire winding and the external metal container (generally made of steel or other similar metals).

The characteristic properties of MgO sands are that of electrically insulating the resistive wire run by electric current and the metal container (generally of a steel nature), as well as those of transmitting by thermal conduction the Joule energy resulting from the ignition of the resistances. (note that we are talking about thermal conduction, not thermal radiation as the present invention).

It is therefore evident that the transmission of the heat of these armored heaters takes place only partially by radiation (irradiation) as it is, and above all, by conduction and convection; the aspect which, however, most differentiates this type of heaters with the invention is represented by the difference in thermal inertia: microtubular heaters are intrinsically subject to a higher thermal inertia with respect to the present invention, which instead does not oppose filters of any kind (the quartz is perfectly transparent to the infrared and ultraviolet radiations), and that it radiates immediately the material in transit in the tube (transparent) its own electromagnetic energy and this happens, also in presence of emptiness, to the speed of the light (same principle of the terrestrial heating originated from the sun).

In fact, by exploiting mainly the postulates of Lambert and Stefan-Boltzmann, today's invention, with the same electrical power applied to the machine, is able to transfer more energy to the materials to be heated, compared to the current state of the art and technique. The thermal conductivity of said MgO and metal container is, on average, estimated at about 50 (W/(m·K)): this is the additional barrier between EMW emitter and material to be treated, if compared with the invention. There are products that use quartz tubes in which to slide the materials to be heated, but the emission source of electromagnetic radiation, also arranged circularly with respect to the aforementioned quartz tube, remains embedded in the "insulating" walls of the artefact, bringing the distance between the emitter and user at several centimetres, thus reducing, at least with quadratic factors, the efficiency of the machine when compared to today's invention.

These observations also apply to those few heating articles which offer a construction technique similar to the present invention, i.e. with the infrared emitter disposed concentrically outside the materials to be treated and which sometimes also use a small translucent quartz central tube inside which run the wires to be heated but which differ from the present invention because of the relatively large distance between the source of emission (resistances) and materials to be heated (we speak at least of a few centimetres). The present invention, having the EMW emission source in contact with the tube in which the materials to be heated is passing, increases the efficiency of the machine with the square of the distance and continuously reflects towards the centre of the gap 6 all the radiation not absorbed immediately from the materials treated with a constant redundant effect.

Description of the Tubular Concentrator by the Concentric Radiation of Electromagnetic Waves The electric machine (fixed, mobile or portable) is used to irradiate a solid, liquid, gaseous or compound matter form, by means of EMWs capable of changing or treating its physical state, using the physical principle of electromagnetic radiation.

According to the basic physical laws, with reference to the efficiency of the reactor, it is important to reduce the distance between the EMW emitter and the treated material as much as possible: the more the distance decreases, the more the efficiency will increase.

The reduction of the distance, associated with the perpendicularity of the emission towards the matter, will exploit the inverse law of the square together with the cosine's Lambertian law.

Moreover, also of topical importance, the device is able to reduce the thickness of the layer of material to be treated, in values even lower than one mm: this fact takes place so as to treat with the radiations also those materials which show accentuated characteristics of reflection: a practical example for everyone can be represented by cow's milk.

Another essential characteristic of the described reactor is represented by the double flow of irradiation which penetrates the material to be treated both from the external side of the tube and from the inside, as can be better appreciated from the drawings.

The flat embodiment, which does not have an inner face since it is not made from a series of concentric tubes 2, 4, but, as can be seen in the images, by two quartz flat glasses, it will show the two emission sources placed outside the flat quartz glasses, in order to concentrate their emissions towards the internal space in which the substances to be treated (liquids, powders, slurries and gases) are passed through.

As said, the device is implemented in different ways but having the same reactor principle:

1. completely tubular with concentric tubes 2, 4 used to divide the various layers in which the material to be treated is irradiated on the internal side and on the external side, since the emitters are positioned below and above the treated material (FIGS. 2-2*e* and FIG. 3-*d*). The device can be miniaturized so that it can be used in a personal way (FIGS. 5-5*e*).

2. Flat device with two round coupling flanges that start the flow towards a central flat part identified as "radiation zone" made with two flat plates 12, 14 of close quartz (FIGS. 4-4*d*), which are coated with the sources of electromagnetic emission on both sides, all in order to obtain a very thin internal area in which the material to be treated can flow. The materials can therefore be easily laminated and irradiated with sub-millimetre thicknesses. The device can be miniaturized so that it can be used in a personal way.

The absence of contacts with the heating bodies (heat generators or electrodes) avoids the typical problems of resistive heaters. The peculiarities of this reactor also concern the possibility of treating those materials that could otherwise be treated by convection or by conduction but with energy yields decidedly lower than the system object of the present patent.

As often said, the machine is highly efficient: it can be easily sensed by observing its peculiar constructive characteristics which are considered useful to list below:

1. the close construction of the walls delimiting the irradiation zone allows to obtain a thickness even lower than the millimetre of the flow to be irradiated, involving an easy penetration of the energy towards the inside of the thickness of the materials flowing into the reactor;

2. the most reflective materials will be the object of continuous irradiation for the reflexivity of the walls of the building which will bounce the reflected energy back to the centre of the gap 6;

3. construction using suitable materials, in particular quartz materials for the transmission of IR and UV energy produced by special irradiators, as well as by reflective sheaths (towards the centre), are designed to contain energy dispersions inside the machine;

4. the invention has only two relatively "small" openings at the inlet and outlet of the system, greatly limiting the dispersion of the energy both by conduction and by convection since all the external surface of the electric machine will be abundantly and suitably insulated or cooled according to needs.

The flexibility of the length of the machine, which each designer can choose according to his own wishes, allows the invention to be used in the most disparate systems, both for the virtual "absence of contact" between materials to be treated and radiating elements, and for the sliding speed of the materials inside, which can also be very high because the transfer of the irradiated energy occurs at the speed of light and varies "only" according to the absorption power of the different materials. It will also be very easy and less expensive than other systems, to run gas in the reaction area at the same time.

Since in physics the elements relevant to the transfer of energy between two bodies, according to the principle of irradiation, are based on a series of variables such as:

i. composition of the matter of bodies
ii. shape of their surface
iii. colour of the surface
iv. irradiated wavelengths
v. irradiation angle
vi. intensity of irradiation the fact of having an EMW emitter disposed on the two sliding surfaces of the material to be treated, allows electromagnetic rays constantly perpendicular to the material to be irradiated, increasing the amount of energy transmitted to the material itself with respect to other treatment systems.

According to an aspect of the invention, the emission points placed outside a cylinder with emission points placed above and below the material to be treated, even of a cylinder, have been replaced, thus also greatly limiting the distance covered by radiation.

This makes it possible to bring the material to be treated very close to the electromagnetic emission source, so as to make the most of the physical postulates (Lambert/Stefan-Boltzmann), gaining efficiency in the electric machine if you want to compare it with other systems radiations which intrude considerably greater distances between emitters and receivers of EMWs or intrude third-party materials, not transparent to radiation but exploiting the principles of thermal conductivity instead of thermal radiation.

Although the electric (static) machine uses components normally used in industry (and not only), for the purposes of electromagnetic radiation, an innovative aspect is the reduction of the thickness of the material to be treated associated with the double emission of the irradiation that hits the material at extremely close range from above and from below, always perpendicularly; all this is associated with the almost complete reflection of the reflected radiations because the system is completely shielded towards the outside.

The particular structure of the invention, with the material to be irradiated placed in the middle of the emitters, allows the same material passing through it, to be always hit perpendicularly by the radiation (IR or UV), thus exploiting the best physical position for the exchange of thermal and UV energy; EMWs reflected inside the enclosure will also contribute significantly to the transfer of energy to the treated material.

Today's invention, in fact, having the emitter of the electromagnetic radiations (IR and UV) that externally surrounds the thin layer (made of transparent IR and UV materials) in which the materials to be treated flow, obtains the following advantages and improvements:

i. the emission points of the radiations are constantly "close" to the materials to be treated (starting from tenths of mm), making the most of the emitted energy available;

ii. the points of radiation strike the material mainly at a perpendicular angle and the radiation is constantly reflected inside the reactor due to the screens placed outside the covering of the radiating emitters;

iii. the section of the material passage volume is perfectly constant and calculable and, during the operation of the machine, every molecule that flows inside the irradiated zone always finds a known maximum and minimum distance, compared to the irradiating source (this fact allows better adjustments and dosages as well as lower consumption);

iv. the proximity of the emitter of the rays to the material that must absorb the radiations (which may even be less than one millimeter) is obtained depending on the thickness of the chosen quartz walls: this means that the energy efficiency of the irradiated energy is much higher if compared to conventional systems;

v. the lack of any interposed wall, beyond the transparent SiO2, allows to drastically reduce the inertias (thermal) that would otherwise be encountered with the systems currently in use.

These particular features allow today's invention to operate with particularly reflective, dirty or otherwise difficult to penetrate electromagnetic radiation.

White liquids such as cow's milk, notoriously difficult to irradiate with normal UV-C systems, find an easy remedy in this invention. Also waste water deriving from water treatment plants, not completely clarified, will find in this invention a useful means of sterilization for recycling the liquids destined for new uses.

Realization

For the realization of this machine it will be necessary: a suitable electric generator calculated on the base of the necessary powers and with the wave generation requests in terms of amplitude and frequency (not shown in the attached drawings) as well as one of the systems listed here:

A) for the concentrically overlapping tube system 2, 4 of which, for example, in FIG. 2 or 3:

two concentric tubes 2, 4 of quartz (SiO2) or substitute material, translucent or transparent and in any case of the material most suitable for the wavelength transparency of the desired rays, having a wall thickness relatively related to use, on which respectively:—for the outermost one 2 of the two concentric ones, wrap the irradiation source on the outer wall (FIGS. 2 and 3) with the emission part facing the inside of the tube;

for the inner one 4, insert inside the tube a cylinder, also empty, on which to wind an EMW emitter with the emission face facing the outside of the tube; the chamber which will form between the two concentric tubes 2, 4, the external one 2 with the emitters on its outside and the internal one with the emitters inside it, will form the gap 6 in which the materials to be treated with the reactor will flow.

B) for the flat system:

the reactor is formed by two flat plates 12, 14 of quartz (SiO2) or substitute material, translucent or transparent and in any case of the material most suitable for the wavelength transparency of the desired radiation, having relatively correlated thicknesses, arranged in parallel and overlapped so as to form a gap 6 between them: the space of the gap 6 will be that dedicated to the material to be treated, while the outer surfaces of the two plates 12, 14 will be coated with resistive materials or single LEDs, SMD or COB, placed with the emitting part directed towards the gap 6, so as to irradiate said gap 6 through its outer walls, since they are transparent to the wavelengths to be used in the reactor.

The rear side of these LED or IR emitters is protected towards the outside by a screen made of a material reflecting the wavelengths used to reflect the radiation towards the material to be treated.

In the case of infrared, the emitters will consist of other appropriate materials in addition to the LEDs.

Beyond the radiation reflecting screen, the reactor will find a device to dissipate excess heat or to save it, depending on the use made of the reactor.

Operation

The materials to be treated will be made transiting inside the gap 6, surrounded above and below by the radiating emitter which operates perpendicular to extremely close distances.

The gap 6, made of a material transparent to the radiations in use, will therefore have completely smooth and very hard walls, of glassy nature (the fused quartz), unassailable by many acids/alkalis also concentrated, and therefore with a long lasting durability. The reflecting screens, placed beyond the emissive layer, will protect the reactor from energy losses and guarantee greater efficiency to the reactor itself; finally, the system dissipating the excess heat or the insulating system will further guarantee the best operation of the apparatus.

The length of the interspaces, the thickness of the tubes, of the resistances, of the powers and frequencies used, of the UV-C LEDs, will be proportional to the quantity of radiated energy and to the mass and nature of materials that must be raised in temperature, as well as the desired temperature delta or the amount of radiation necessary for sterilization processes; all according to the designed transit speeds.

It is more than obvious as regards the IR treatment, that a part of the energy useful for heating will reach the materials to be heated, not only by irradiation (and induction), but by convection.

Whilst operating, the double radiation combined with the proximity of the radiators to the material being subjected to the radiation, will allow a better efficacy as well as the operation also with those reflecting or difficult to penetrate materials.

Utility

The usefulness of the reactor, thus conceived, is evident in the possibility to treat materials having different physical forms, mainly liquids and gases but also micronized solids or mixtures of such materials and, with respect to the known current technique, obtain the following contemporary benefits:

vii. the materials to be treated are very close to the source of emission of electromagnetic radiations but never come into contact with them;

viii. the treated materials are no longer the object of the well-known unwanted physical modifications of the treated materials such as for example the electric arcs or other problems typical of the electrodes;

ix. the same plant can alternatively treat a variety of materials without having to change the heating or treatment machines. In other words, conductive and non-conductive materials and can be treated in the same plants.

x. the adjustments will be easier and more immediate because, by exploiting the irradiation prevalently to the convection and conduction systems, the important inertiae that is physically interposed in conventional plants are almost canceled with those detectable in the invention which can instead be defined as "residual" as they are without any contact with the physical parts of the "radiant" source.

xi. the current sliding speeds of industrial plants that will use radiation systems such as those described here will not be reduced, but increases simply by adapting the reactors to real production needs;

xii. for the conception and the forms of the construction of the machine itself an important energy saving is expected: it derives from the close proximity of the emitter with respect to the receiving material, combined with the perpendicularity of the rays, the reflection of the same, associated with the possibility of an efficient insulation of the whole (therefore to the heat and to the EMWs) making sure that the energy—radiated in great prevalence—remains constipated inside the electric machine itself that, so insulated outside, of small mass and very small openings to the entry and exit, allows a very high efficiency of the energy used, compared to conventional and non-conventional systems known today.

xiii. As far as UV rays are concerned, the treatments carried out with the thin film irradiation system, with close proximity, improve the current state of the art:

a) increasing the specific energy irradiated per unit of surface (and therefore of volume);

b) eliminating the problems related to reflecting materials or dirty materials that would not allow thicknesses otherwise used in normal tubes;

c) spreading the UV-C rays, only where they are needed;

d) irradiating the materials mainly in a perpendicular way.

For an idea of practical application, among many we can think of a milk treatment plant that, without the use of steam, succeeds, on the same line, both to perform the UHT treatment (by IR) and sterilization (through UV) and all this in much smaller spaces and a very low energy waste generated by the dispersion of the systems (i.e. steam system that provides a heat exchange at the origin and one in the exchanger with milk in addition to energy loss in the steam transport). As regards more conventional applications, the following is a summary list that is not exhaustive but only relatively explanatory:

i. instantaneous hot water heaters;

ii. in-line process air/gas heaters;

iii. instantaneous steam producers;

iv. disinfection of clean and opaque water;

v. sterilization of milk;

vi. sterilization of beverages such as beer, wine or fruit smoothies;

vii. UHT treatment facilities;
viii. industrial liquid sterilizers;
ix. tubular flash pasteurization;
x. industrial sterilizer in-line
xi. portable solar field sterilizer for drinking water.

LIST OF REFERENCE NUMBERS 1 tubular reactor
1' tubular reactor
2 outer tube
4 inner tube
6 gap
8 internal source
10 external source
12 flat plate
14 flat plate
16 profile
18 profile
20 lamellar reactor
20' reactor
22 reflector
24 reflector
26 transportable casing
28 cylindrical end portions
30 disinfection device
32 central portion
34 offset inlet
36 coupling flange, in particular round
38 water inlet
40 water outlet
42 USB auxiliary power input
44 USB auxiliary power output
46 UV-C LED emitters
48 UV-C LED emitters
50 screen
52 screen
54 anchor slide
56 anchor slide
58 anchor slide
60 solar cell
62 solar panel
64 battery
66 interlocking slot
68 interlocking slot
70 sealing gasket
72 sealing gasket
74 sealing gasket between flange and quartz tubes
76 perforated flange for the passage of water and cooling air inside heat-sink
78 annular air distribution chamber to produce Coanda effect on heat sink
80 compressed air inlet tube connected to annular chamber 78
82 water
84 bolt
86 high-speed cooling air slot, creating an amplification of the phenomenon by Coanda effect
88 compressed air inlet tube connected to slot 86
90 cooling air passage hole; preferably, this hole is optimized to allow greater efficiency in the Coanda effect;
92 seal
94 screw
L longitudinal direction

The invention claimed is:

1. Tubular reactor (1, 1') for irradiation of EMWs (ElectroMagnetic Waves) with a substantially cylindrical shape, comprising:
a pair of concentric tubes (2, 4) extending in a longitudinal direction (L) and comprising an outer tube (2), defined by an inner wall of outer tube (2) and by an outer wall of outer tube (2), and an inner tube (4), defined by an inner wall of inner tube and by an outer wall of inner tube, said outer and inner tubes being made of transparent material to the EMWs, being open at both ends, and forming a gap (6) defined by the inner wall of outer tube (2) and by the outer wall of inner tube (4), said gap being suitable for the passage of a material to be treated, in solid, liquid, gaseous and/or powdery form;
a pair of opposed EMW emission sources, comprising an external source (10) and an internal source, said external and internal sources comprising each at least one EMW emitter, the external source (10) winding the outer wall of outer tube (2) with the EMW emission face of the external source facing the inside of the reactor, the internal source (8) winding the inner wall of inner tube with the EMW emission face of the internal source facing the outside of the reactor, said emission sources emitting EMWs with wavelengths comprised between the ultraviolet rays (UV) and infrared (IR) rays, in order to radiate perpendicularly, with respect to the longitudinal direction (L) of development of the reactor, the material to be treated flowing in the gap (6).

2. Lamellar reactor (20, 20') for irradiation of EMWs (ElectroMagnetic Waves) comprising:
a pair of flat plates (12, 14) of rectangular shape and extending in a longitudinal direction (L), said flat plates (12, 14) being made of transparent material to the EMWs, and being arranged without contact one above the other by means of a pair of profiles (16, 18) suitable for engaging with the longitudinal edges of the flat plates (12, 14), said flat plates (12, 14) and said profiles (16, 18) delimiting an external portion to the reactor and an internal portion to the reactor, said internal portion defining a gap open at both ends and suitable for the passage of a thin film of a material to be treated, in a solid, liquid, gaseous and/or powdery form;
a pair of opposed EMW emission sources, said sources covering the surface of the pair of flat plates (12, 14) defining the external portion of the reactor and emitting EMWs towards the internal portion of the reactor, so as to radiate perpendicularly to the longitudinal direction (L) of development of the reactor, the gap where the material to be treated flows, with EMWs of wavelengths between ultraviolet (UV) and infrared (IR) rays.

3. Reactor according to claim 1 or 2, comprising a pair of reflectors made of a material having a reflection coefficient of the EMWs ranging from 0.5 to 1, wherein the pair of reflectors is made of a material having a thermal conductivity lower than 5 W/m: K calculated at 20° C., and wherein a first reflector of said pair of reflectors covers a first emission source of the pair of emission sources and wherein the second reflector of said pair of reflectors covers the second emission source of the pair of emission sources, said first and second reflectors being suitable for the reflection of the EMWs towards the gap.

4. Reactor according to claim 1 or 2, in which the emission sources radiate EMWs with wavelengths different from one another.

5. Reactor according to claim 1 or 2, in which the distance between the material to be treated and any of the two emission sources is comprised between 50 micrometers and 30 millimeters.

6. Reactor according to any of the preceding claim 1 or 2, in which the concentric tubes (2, 4) or flat plates (12, 14) have a thickness less than or equal to 1 millimeter.

7. Reactor according to any of the preceding claim 1 or 2, in which each EMW emission source comprises a plurality of EMW emitters arranged so as to form an emission layer.

8. Device for the disinfection (30) of fluids made inside a transportable casing (26) comprising a tubular reactor (1, 1') and/or a lamellar reactor (20, 20') according to any of the preceding claim 1 or 2 (addition) and suitable electric power supplies for the operation of said reactors (1, 1', 20, 20',).

* * * * *